United States Patent
Nagano et al.

(10) Patent No.: US 6,201,134 B1
(45) Date of Patent: Mar. 13, 2001

(54) DIAMINORHODAMINE DERIVATIVES

(75) Inventors: Tetsuo Nagano; Hirotatsu Kojima, both of Tokyo (JP)

(73) Assignee: Tetsuo Nagano, Tokyo (JP)

( * ) Notice: Subject to any disclaimer, the term of this patent is extended or adjusted under 35 U.S.C. 154(b) by 0 days.

(21) Appl. No.: 09/446,899

(22) PCT Filed: Jun. 30, 1998

(86) PCT No.: PCT/JP98/02924

§ 371 Date: Apr. 3, 2000

§ 102(e) Date: Apr. 3, 2000

(87) PCT Pub. No.: WO99/01447

PCT Pub. Date: Jan. 14, 1999

(30) Foreign Application Priority Data

Jul. 2, 1997 (JP) .................................................. 9/177097

(51) Int. Cl.[7] ........................ C07D 311/88; C07D 403/00
(52) U.S. Cl. ........................................... 549/227; 548/261
(58) Field of Search ............................... 549/227; 548/261

(56) References Cited

PUBLICATIONS

Kojima et al., the 16th Medicinal Chemikstry Sumposium, the 5th Annual Meeting of the Pharmaceutical Chemistry Section, the Lecture Abstracts, pp. 165–167, Subject No. 2–P–26, published by the Pharmaceutical Society of Japan, Oct. 23, 1996.
Maeda, H., et al., J. Leuk. Biol., 56, pp. 588–592, 1994.
Akaike T., et al., Biochemistry, 32, pp. 827–832, 1993.
FEBS Lett., 427[2](1998) p. 263–266.
Anal. Chem., 70[13 ](1998) p. 373–375.
Chem. Pharm. Bull., 46[2](1998) p. 373–375.
English Language Abstract of JP 9–43153.
Chemistry Today [Gendai Kagaku], Apr. 1994.*
Special Edition; Pharmacia, May, 1997.*
Palmer R. M., et al., Nature 327, pp. 524–526, 1987.*
Kelm M., et al., Circ. Res. 66, pp. 1561–1575, 1990.*
Shibuki K., Neurosci. Res. 9, pp. 69–76, 1990.*
Malinski, and T., Nature, 358, pp. 676–678, 1992.*
Green L.C., et al., Anal. Biochem., 126, pp. 131–138, 1992.*
Archer, S., Faseb J., 7, pp. 349–360, 1993.*
Stainton M.P., Anal Chem., 46, p. 1616, 1974.*
Sawicki, C.R. and Scaringelli, F.P., Microchem. J., 16; pp. 657–672, 1971.*
Wiersma J.H., Anal Lett., 3, pp. 123–132, 1970.*
Sawicki, C.R., Anal. Lett., 4, pp. 761–775, 1971.*
Damaiani, P. and Burini, G., Talanta, 8, pp. 649–652, 1986.*
Misko, T.P., Anal. Biochem. 214, pp. 11–16, 1993.*
DOJIN News, No. 74, Information Measurement Reagents for NO: 2,3–Diaminonaphthalene, published by Dojindo Laboratories Co., Ltd., 1995.*

* cited by examiner

Primary Examiner—Amelia Owens
(74) Attorney, Agent, or Firm—Greenblum & Bernstein P.L.C.

(57) ABSTRACT

A compound represented by the following general formula:

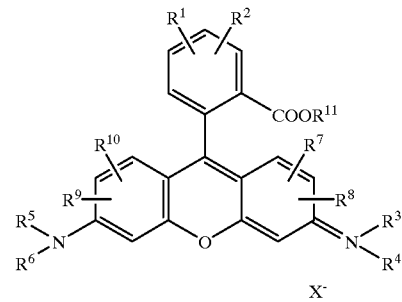

wherein $R^1$ and $R^2$ represent amino groups present at adjacent positions each other on the phenyl ring; $R^3$, $R^4$, $R^5$ and $R^6$ independently represent a $C_{1-6}$ alkyl group; $R^7$, $R^8$, $R^9$ and $R^{10}$ independently represent a hydrogen atom, a $C_{1-6}$ alkyl group, an allyl group, or a halogen atom; $R^{11}$ represents a hydrogen atom or a $C_{1-18}$ alkyl group; and $X^-$ represents an anion, and an agent for nitric oxide measurement comprising said compound.

The compound efficiently reacts with nitric oxide to give a fluorescent compound that emits strong fluorescence by irradiation with excitation light of a long wavelength. This fluorescent compound is characterized in that said compound is detectable in a fluorescence wavelength range hardly influenced by autofluorescence of cells, and its fluorescence intensity is not attenuated under an acidic condition.

5 Claims, 5 Drawing Sheets

DIAMINORHODAMINE DERIVATIVES

TECHNICAL FIELD

The present invention relates to a rhodamine derivatives useful as a reagent for measurement of nitric oxide, and a reagent for nitric oxide measurement which comprises said compound.

BACKGROUND ART

Nitrogen monoxide (NO) is an unstable radical species of a short life, and has been elucidated to have important functions as a physiological active substance in a living body (Chemistry Today [Gendai Kagaku], April, 1994, Special Edition; Pharmacia, May, 1997, Special Edition). Methods for measuring nitric oxide are roughly classified into indirect methods, which measure $NO_2^-$ and $NO_3^-$ as oxidative degradation products of nitric oxide, and methods based on direct measurement of nitric oxide. The direct methods have been eagered from viewpoints of detection and quantification of nitric oxide under physiological conditions. However, any specific and highly sensitive detection method that can be applied to in vitro systems has not been developed so far.

As typical methods, there have been known, for example, the chemiluminescence method utilizing the luminescence generated by ozone oxidation of NO radicals (Palmer R. M., et al., Nature, 327, pp.524–526, 1987), a method determining absorption spectrum of metHb which is produced by oxidation of oxyhemoglobin ($O_2Hb$) (Kelm M., et al., Circ. Res. 66, pp.1561–1575, 1990), a method for quantification utilizing the flow of electric current produced in oxidation when electrodes are placed in a tissue (Shibuki K., Neurosci. Res. 9, pp.69–76, 1990; Malinski, and T., Nature, 356, pp.676–678, 1992), the Griess reaction method (Green L. C., et al., Anal. Biochem., 126, pp.131–138, 1992) and so forth (as reviews, see, "Approaches From The Newest Medicine [Saishin Igaku Kara No Approach] 12, NO", Ed. by Noboru Toda, pp.42–52, Section 3, Tetsuo Nagano, Measuring Method of NO, published by Medical View Co., Ltd; Archer, S., FASEB J., 7, pp.349–360, 1993).

The Griess reaction method achieves the detection by using azo coupling of a diazonium salt compound and naphthylethylenediamine in the presence of $NO_2^-$ that is produced by oxidation of a nitric oxide radical. Although this method does not achieve direct measurement of nitric oxide radicals, the method has the merit of requiring no special apparatuses or techniques. Moreover, this method also has a characteristic feature that nitric oxide-related metabolites can be quantified, since $NO_3^-$ can be measured by reduction to $NO_2^-$ with cadmium (Stainton M. P., Anal. Chem., 46, p.1616, 1974; Green L. C., et al., Anal. Biochem., 126, pp.131–138, 1982) or hydrazine (Sawicki, C. R. and Scaringelli, F. P., Microchem. J., 16, pp.657–672, 1971).

As a reagent for measuring nitric oxide by detecting $NO_2^-$ in a similar manner to the Griess reaction method, 2,3-diaminonaphthalene has been known. This reagent reacts with $NO_2^-$ under acidic conditions to form a fluorescent adduct, naphthalenetriazole (chemical name: 1-[H]-naphtho [2,3-d]triazole, Wiersma J. H., Anal. Lett., 3, pp.123–132, 1970). The conditions for the reaction of 2,3-diaminonaphthalene with $NO_2^-$ have been studied in detail, demonstrating that the reaction proceeds most quickly at pH 2 or lower and completes in approximately 5 minutes at room temperature (Wiersma J. H., Anal. Lett., 3, pp. 123–132, 1970; Sawicki, C. R., Anal. Lett., 4, pp.761–775, 1971). Furthermore, the generated adduct emits fluorescence most efficiently at pH 10 or higher (Damiani, P. and Burini, G., Talanta, 8, pp.649–652, 1986).

The measurement of nitric oxide using the 2,3-diaminonaphthalene is characterized in that a detection limit is about several tens nanomoles and sensitivity is 50 to 100 times higher than that of the Griess reaction method (Misko, T. P., Anal. Biochem. 214, pp.11–16, 1993). Moreover, the method is also excellent in that it can be carried out conveniently without requiring any special apparatuses or techniques (as a review of the above description, see, DOJIN News, No. 74, Information Measurement Reagents for NO: 2,3-Diaminonaphthalene, published by Dojindo Laboratories Co., Ltd., 1995). However, since this method does not utilizes nitric oxide, per se, but its oxidation product, $NO_2^-$, as the reaction species, the method is rather indirect as compared to the direct method for measuring nitric oxide. In addition, since the reaction of 2,3-diaminonaphthalene and $NO_2^-$ is performed under strongly acidic conditions (pH 2 or lower), it has a problem that the method cannot be available for detection and quantification of nitric oxide under a physiological condition.

The inventors of the present invention conducted researches to provide means for direct measurement of nitric oxide with high sensitivity under a physiological condition. As a result, the inventors found that 2,3-diaminonaphthalene or derivatives thereof efficiently reacts with nitric oxide to give fluorescent naphthalenetriazole or its derivatives, even under a neutral condition, in the presence of an oxygen source such as dissolved oxygen or oxide compounds (for example, PTIO and its derivatives such as carboxy-PTIO). Moreover, the inventors also found that a method for measuring nitric oxide employing this reaction gave extremely high detection sensitivity and achieved accurate quantification of a trace amount of nitric oxide (see, the specification of Japanese Patent Application No. 7 189978/1995).

However, the aforementioned method utilizing 2,3-diaminonaphthalene needs irradiation by excitation light of a short wavelength such as about 370 to 390 nm for the detection of fluorescence, and accordingly, cells and tissues in a measurement system may possibly be damaged. The method also has a problem in that strong autofluorescence of cells may affect the measurement and, in the fluorescence measurement, excitation light cannot be sufficiently cut with a fluorescence filter equipped on usual fluorescence microscopes. Moreover, the fluorescent triazole compound produced from 2,3-diaminonaphthalene does not have sufficient fluorescence intensity and, for this reason, it is difficult to accurately measure fluorescence in individual cells by conventional fluorescence microscopes. In addition, there is also a problem that 2,3-diaminonaphthalene itself is not suitable as a basic structure for various chemical modification so that the reagent can be localized inside of cells because of its simple chemical structure.

It has recently been reported that certain fluorescein derivatives, which themselves do not emit substantial fluorescence, can readily react with nitric oxide under a neutral condition to form a triazole compound exhibiting fluorescence of high intensity, and the triazole derivative can emit strong fluorescence of about 515 nm by means of long wavelength excitation light of approximately 495 nm (Kojima et al., the 16th Medicinal Chemistry Symposium, the 5th Annual Meeting of the Pharmaceutical Chemistry Section, the Lecture Abstracts, pp.166–167, Subject No. 2-P-26, published by the Pharmaceutical Society of Japan, Oct. 23, 1996).

When these fluorescein derivatives are used as an agent for measurement of nitric oxide, excitation light can be easily cut by a fluorescence filter provided on usual fluorescence microscopes, and intracellular nitric oxide concentration can easily be measured by observing fluorescence in individual cells. However, the fluorescence wavelength range of the aforementioned fluorescein derivatives partly overlaps with the autofluorescence wavelength range of cells and, accordingly, it may sometimes be impossible to accurately quantify nitric oxide. Moreover, since the fluorescence may be attenuated under acidic conditions (e.g., pH 4 or lower), there is also a problem that accurate measurement cannot be performed in a wide pH range.

DISCLOSURE OF THE INVENTION

An object of the present invention is to provide a compound useful for the measurement of nitric oxide. More specifically, the object of the present invention is to provide a compound that can efficiently react with nitric oxide under a neutral condition to give a fluorescent substance excellent in the fluorescence intensity. Another object of the present invention is to provide a compound which has the aforementioned characteristics and enables measurement of nitric oxide in a fluorescence wavelength range longer than that of the autofluorescence wavelength range of cells without damaging tissues or cells of living body. Furthermore, a further object of the present invention is to provide a compound that has the aforementioned characteristics and does not attenuate fluorescence even in an acidic condition. A still further object of the present invention is to provide an agent for nitric oxide measurement which comprises a compound having the aforementioned characteristics, more specifically, an agent for nitric oxide measurement which enables accurate measurement of nitric oxide present in the inside of each individual cell.

The inventors of the present invention conducted earnest researches to achieve the foregoing objects. As a result, they found that the rhodamine derivatives mentioned below can efficiently react with nitric oxide under a neutral condition to give triazole derivatives having excellent fluorescence intensity. Furthermore, they also found that the wavelength range of fluorescence of those triazole derivatives sifted to longer wavelength range compared with the fluorescein derivatives (16th Medicinal Chemistry Symposium, the Lecture Abstracts, as described above) and did not substantially overlap with the autofluorescence wavelength range of cells, and that the triazole derivatives exhibited no decrease in intensity of fluorescence even under an acidic condition. The present invention was achieved on the basis of these findings.

The present invention thus provides compounds represented by the following formula (I):

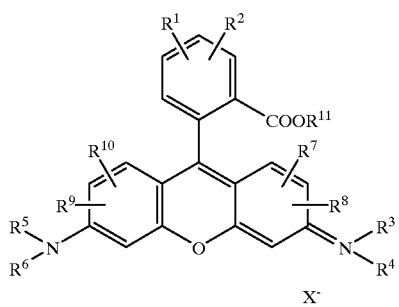

wherein $R^1$ and $R^2$ represent amino groups present at adjacent positions each other on the phenyl ring; $R^3$, $R^4$, $R^5$ and $R^6$ each independently represent a $C_{1-6}$ alkyl group; $R^7$, $R^8$, $R^9$ and $R^{10}$ each independently represent a hydrogen atom, a $C_{1-6}$ alkyl group, an allyl group, or a halogen atom; $R^{11}$ represents a hydrogen atom or a $C_{1-18}$ alkyl group; and $X^-$ represents an anion. According to a preferred embodiment of the aforementioned compounds, there are provided the aforementioned compounds wherein $R^3$, $R^4$, $R^5$ and $R^6$ are ethyl groups; and $R^7$, $R^8$, $R^9$ and $R^{10}$ are hydrogen atoms. Furthermore, as another aspect of the present invention, there are provided agents for nitric oxide measurement comprising the aforementioned compounds.

As another aspect of the present invention, there are provided compounds represented by the following formula (II):

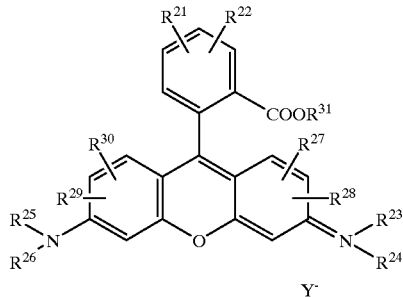

wherein $R^{21}$ and $R^{22}$ are present at adjacent positions on the phenyl ring and bind to each other to form a group represented by $-N=N-NR^{41}-$ that forms a ring, wherein $R^{41}$ represents hydrogen atom, a $C_{1-18}$ alkyl group, or an aralkyl group which may be substituted, or $R^{21}$ and $R^{22}$ represent a combination of amino group and nitro group present at adjacent positions on the phenyl ring; $R^{23}$, $R^{24}$, $R^{25}$ and $R^{26}$ each independently represent a $C_{1-6}$ alkyl group; $R^{27}$, $R^{28}$, $R^{29}$ and $R^{30}$ each independently represent a hydrogen atom, a $C_{1-6}$ alkyl group, an allyl group, or a halogen atom; $R^{31}$ represents a hydrogen atom or a $C_{1-18}$ alkyl group; and $Y^-$ represents an anion. According to a preferred embodiment of the aforementioned compounds, there are provided the aforementioned compounds wherein $R^{23}$, $R^{24}$, $R^{25}$ and $R^{26}$ are ethyl groups; and $R^{27}$, $R^{28}$, $R^{29}$ and $R^{30}$ are hydrogen atoms.

Furthermore, as a still further aspect of the present invention, there is provided a method for measuring nitric oxide, which comprises the steps of (1) allowing a compound represented by the aforementioned formula (I) to react with nitric oxide, and (2) detecting a compound of the formula (II) produced in the aforementioned step (1).

BEST MODE FOR CARRYING OUT THE INVENTION

Figure 1:
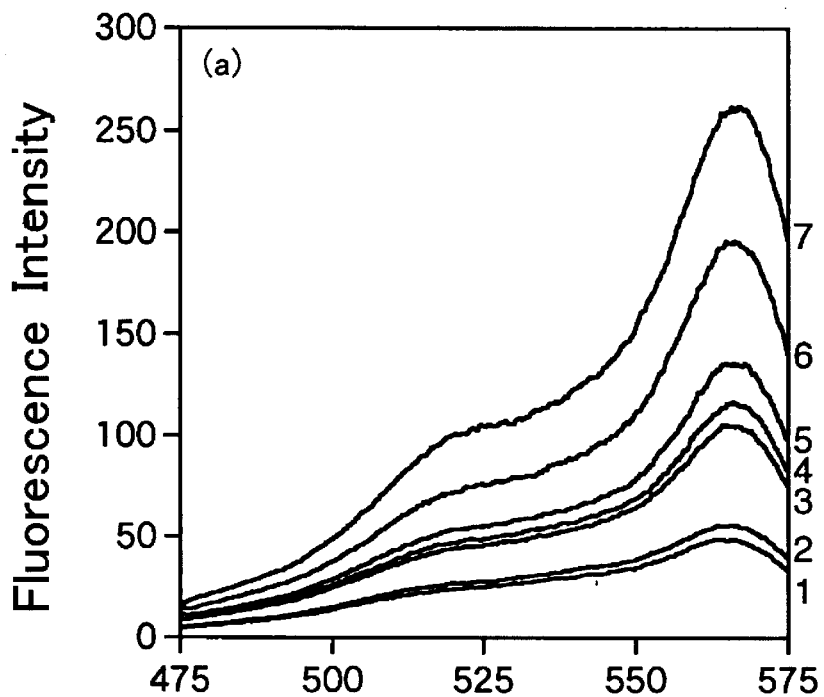
FIG. 1 depicts changes in fluorescence spectra of a compound of the formula (I) after the addition of nitric oxide. In the figure, (a) represents an excitation spectrum (Em. 580 nm), and (b) represents a fluorescence spectrum (Ex. 565 nm). The concentrations of nitric oxide were 1: 0.11 μM, 2: 0.21 μM, 3: 0.32 μM, 4: 0.43 μM, 5: 0.53 μM, and 6: 0.64 μM.
Figure 1:
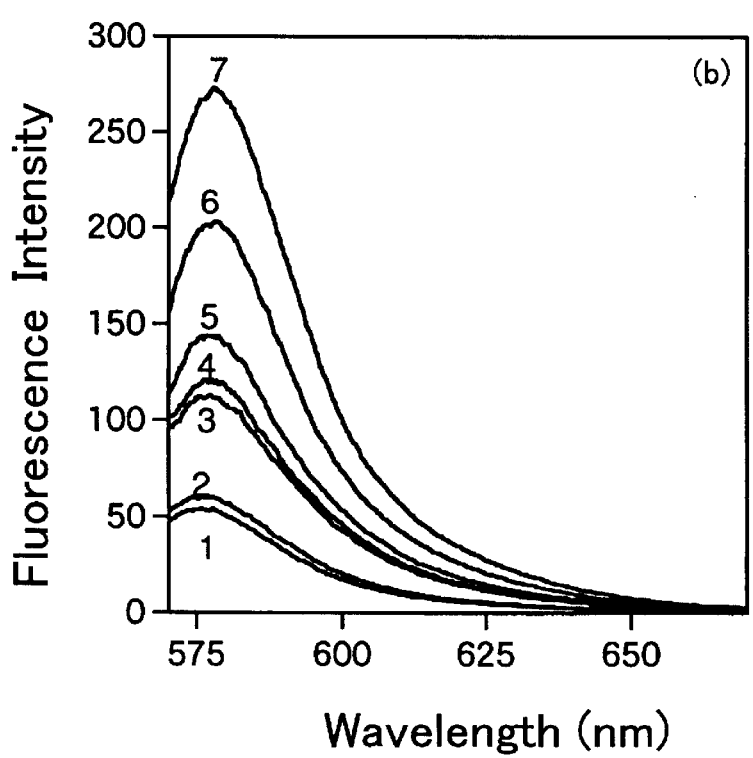

In the aforementioned general formula (I), $R^1$ and $R^2$ represent amino groups that substitute at adjacent positions on the phenyl ring. Both of $R^1$ and $R^2$ are preferably non-substituted amino groups, or either of $R^1$ and $R^2$ may be a monosubstituted amino group. Examples of the substituent present on the amino group include, for example, a linear or branched $C_{1-18}$ alkyl group (preferably, a $C_{1-6}$ alkyl group), a $C_{1-6}$ alkyl group substituted with an optionally-substituted aryl group (aralkyl group) and the like. In the specification, the $C_{1-6}$ alkyl may be linear or branched unless otherwise specifically indicated. Specific examples thereof include, for example, methyl group, ethyl group, n-propyl group, iso-propyl group, n-butyl group, sec-butyl group, tert-butyl group. Examples of the aryl-substituted alkyl group include, for example, benzyl group, phenethyl group, p-methoxybenzyl group, p-ethoxycarbonylbenzyl group, p-carboxybenzyl group.

$R^3$, $R^4$, $R^5$ and $R^6$ each independently represent a $C_{1-6}$ alkyl group, and alkyl groups for these groups may be the same or different. For example, compounds wherein $R^3$, $R^4$, $R^5$ and $R^6$ are ethyl groups are preferred embodiment of the present invention. $R^{11}$ represents a hydrogen atom or a $C_{1-18}$ alkyl group, preferably a $C_{1-6}$ alkyl group, more preferably hydrogen atom or ethyl group, and most preferably hydrogen atom. Kinds of the anion represented by $X^-$ are not particularly limited. For example, a halogen ion such as chlorine ion and bromine ion, inorganic acid ion such as sulfate ion, nitrate ion and perchlorate ion, an organic acid ion such as methanesulfonate ion, p-toluenesulfonate ion, oxalate ion, citrate ion or the like may be used.

$R^7$, $R^8$, $R^9$ and $R^{10}$ each independently represent hydrogen atom, a $C_{1-6}$ alkyl group, an allyl group ($CH_2=CH-CH_2-$), or a halogen atom. The halogen atom may be any one of fluorine atom, chlorine atom, bromine atom, and iodine atom, and may preferably be chlorine atom. Positions of substituents selected from the group of $R^7$, $R^8$, $R^9$ and $R^{10}$ are not particularly limited. A substituent other than a hydrogen atom may preferably substitute at a position selected from 2-, 4-, 5- and 7-positions of the xanthene structure. For example, it is preferred that each of $R^7$, $R^8$, $R^9$ and $R^{10}$ is hydrogen atom.

In the aforementioned formula (II), $R^{21}$ and $R^{22}$ may bind to each other to represent a group $-N=N-NR^{41}-$ that forms a ring at adjacent positions on the phenyl ring. $R^{41}$ represents hydrogen atom, a linear or branched $C_{1-18}$ alkyl group (preferably, a $C_{1-6}$ alkyl group), or a $C_{1-6}$ alkyl group substituted with an optionally-substituted aryl group. Examples of the aryl-substituted alkyl group include, for example, benzyl group, phenethyl group, p-methoxybenzyl group, p-ethoxycarbonylbenzyl group, p-carboxybenzyl group. Alternatively, $R^{21}$ and $R^{22}$ represent a combination of amino group and nitro group which substitute adjacent positions of the phenyl ring, namely, one of $R^{21}$ and $R^{22}$ represents amino group, and the other represents nitro group. The amino group represented by $R^{21}$ or $R^{22}$ may be non-substituted amino group, or may have one substituent such as a $C_{1-18}$ alkyl group (preferably, a $C_{1-6}$ alkyl group) and the aforementioned $C_{1-6}$ alkyl group substituted with an optionally-substituted aryl group. The amino group may have a protective group such as, for example, an acyl group such as acetyl group, trifluoroacetyl group, and benzoyl group; an alkylsilyl groups such as trimethylsilyl group and the like. An arylalkyl group such as benzyl group may also be used as the protective group.

$R^{23}$, $R^{24}$, $R^{25}$ and $R^{26}$ each independently represent a $C_{1-6}$ alkyl group, and the alkyl groups represented by these groups may be the same or different. For example, compounds wherein $R^{23}$, $R^{24}$, $R^{25}$ and $R^{26}$ are ethyl groups are preferred embodiments of the present invention. $R^{31}$ represents hydrogen atom or a $C_{1-18}$ alkyl group, preferably a $C_{1-6}$ alkyl group, more preferably hydrogen atom or ethyl group, and most preferably hydrogen atom. Kinds of the anion represented by $Y^-$ are not particularly limited. For example, a halogen ion such as chlorine ion and bromine ion, inorganic acid ion such as sulfate ion, nitrate ion and perchlorate ion, an organic acid ion such as methanesulfonate ion, p-toluenesulfonate ion, oxalate ion, citrate ion or the like may be used.

$R^{27}$, $R^{28}$, $R^{29}$ and $R^{30}$ each independently represent hydrogen atom, a $C_{1-6}$ alkyl group, an allyl group, or a halogen atom. The halogen atom may be any one of fluorine atom, chlorine atom, bromine atom and iodine atom, and may preferably be chlorine atom. Positions of substituents selected from $R^{27}$, $R^{28}$, $R^{29}$ and $R^{30}$ are not particularly limited. A substituent other than hydrogen atom may preferably substitute at a position selected from 2-, 4-, 5- and 7-positions of the xanthene structure. For example, it is preferred that each of $R^{27}$, $R^{28}$, $R^{29}$ and $R^{30}$ is hydrogen atom.

The compounds of the aforementioned formulas (I) and (II) wherein $R^{21}$ and $R^{22}$ represent a combination of amino group and nitro group at adjacent positions on the phenyl ring can be prepared, for example, according to the following scheme, and the details thereof will be specifically described in the examples mentioned in the present specification. Therefore, it will be understood that the compounds of the aforementioned formula (II) are useful as synthetic intermediates of the compounds of the formula (I). Furthermore, among the compounds represented by the formula (II), those wherein $R^{21}$ and $R^{22}$ bind to each other to form a group represented by $-N=N-NR^{41}-$ that forms a ring at adjacent positions on the phenyl ring can be produced by allowing a compound of the aforementioned formula (I) to react with nitric oxide. Those compounds have strong fluorescence as will be described below, and are useful for the measurement of nitric oxide.

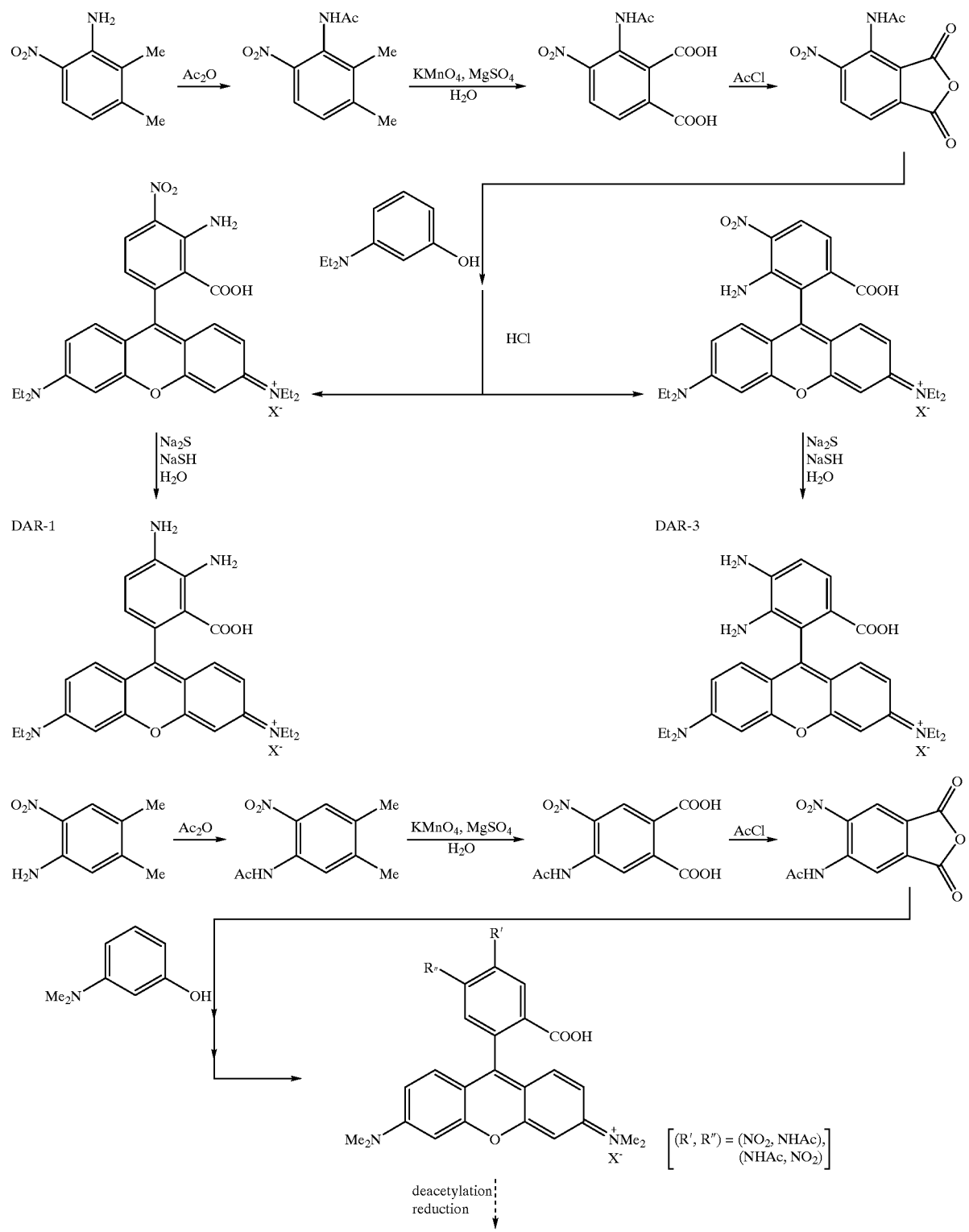

-continued

DAR-2

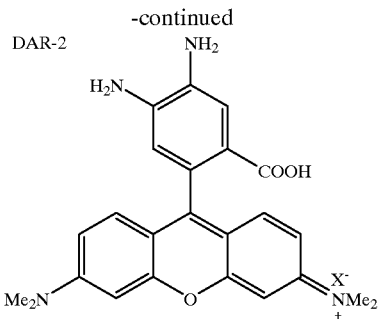

It will be understood by those skilled in the art that any compounds represented by the formulas (I) and (II) can readily be prepared by referring to the general explanation in the aforementioned scheme and specific description in the examples. Methods for preparing rhodamine derivatives having various substituents are known, and accordingly, any compounds represented by the formulas (I) and (II) can be readily prepared by combining known preparation methods available to those skilled in the art and the methods mentioned in the examples of the specification. The compounds represented by the formulas (I) and (II) of the present invention may have one or more asymmetric carbon atoms. Any optical isomers deriving from one or more asymmetric carbon atoms, those in an optically pure form, any mixtures of optical isomers, racemates, diastereoisomers in pure form, mixtures of diastereoisomers and so forth all fall within the scope of the present invention. Furthermore, the compound of the present invention may exist as a hydrate or a solvate, and it should be understood that these substances also fall within the scope of the present invention.

Furthermore, it is known that rhodamine derivatives may form a lactone ring and exist as compounds in a free form. Among the compounds of the present invention represented by the formulas (I) and (II), it will be readily understood by those skilled in the art that compounds of which $R^{11}$ and $R^{31}$ are hydrogen atoms may exist in structural isomers forming a lactone ring. It should be understood that those structural isomers also fall within the scope of the present invention (it will also be readily understood by those skilled in the art that a quaternary amino group does not exist in such compounds, and hence the anion represented by $X^-$ or $Y^-$ that serves as a counter ion does not exist). The compounds forming a lactone ring included in the present invention are represented by the following formulas (I)' and (II)' (these compounds correspond to those represented by the formulas (I) and (II), respectively, and $R^1$ to $R^{10}$ and $R^{21}$ to $R^{30}$ have the same meanings as defined above). As the aforementioned formulas (I) and (II), as well as those in the aforementioned scheme, only the compounds that do not form a lactone ring are defined for the sake of convenience. Furthermore, it will also be readily understood by those skilled in the art that those not having $R^{11}$ or $R^{31}$ but having carboxyl anion may form an intramolecular zwitterion and neutralize its charge with the positive electric charge of the quaternary amino group, and hence such compounds do not have an anion represented by $X^-$ or $Y^-$ that serves as a counter ion. It should be understood that such compounds also fall within the scope of the present invention.

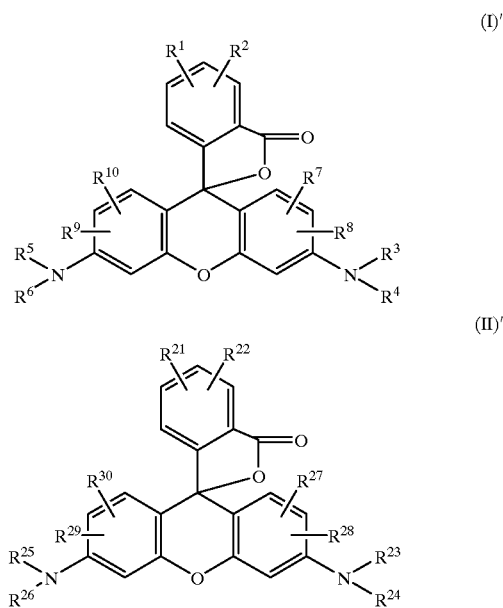

The compounds represented by the formula (I) of the present invention have a property that they efficiently react with nitric oxide under a neutral condition to give a compound of the formula (II) in a good yield (a compound in which $R^{21}$ and $R^{22}$ are present at adjacent positions each other on the phenyl ring and bind to each other to form a group represented as —N=N—NR$^{41}$— that forms a ring). The compounds represented by the formula (I) themselves do not emit substantial fluorescence when they are irradiated by excitation light at about 565 nm under a neutral condition, whilst the compounds of the formula (II) emit extremely strong fluorescence under the same condition (emission: 580 nm). Therefore, nitric oxide in the living tissues or cells can be measured by allowing the compounds represented by the formula (I) to be incorporated into living tissues or cells and to react with nitric oxide to generate fluorescent compounds of the formula (II), and then measuring fluorescence of the resulting compounds. In particular, because the fluorescence wavelength range of the compounds of the formula (II) of the present invention is shifted to longer wavelength side by about 80 nm compared to conventional known fluorescein derivatives, they have an excellent characteristic that they enable the fluorescence measurement without being influenced by autofluorescence of cells.

The method for measuring nitric oxide provided by the present invention thus comprises steps of allowing a compound represented by the formula (I) to react with nitric oxide to form a compound of the formula (II), and then measuring the fluorescence of the compound of the formula (II) (a compound in which $R^{21}$ and $R^{22}$ are present at adjacent positions on the phenyl ring and bind to each other to represent the group —N=N—NR$^{41}$— that forms a ring). In the specification, the term "measurement" should be construed in its broadest sense including measurement for various purposes such as detection, quantitative and qualitative determinations. The aforementioned reaction can preferably be performed under a neutral condition, for example, within a range of pH 6.0 to 8.0, preferably pH 6.5 to 7.8, more preferably pH 6.8 to 7.6. In particular, the compounds represented by the formula (II) of the present invention have a characteristic feature that their fluorescence is not attenuated under a weakly acidic condition, preferably in an acidic pH range of down to pH 4. However, the measurement of nitric oxide using the compounds of the present invention is not limited to measurement under a neutral condition or a weakly acidic condition, and the measurement can also be performed under a strongly acidic condition, for example, a condition surrounding gastric mucosal cells and the a like.

Among the compounds of the formula (I), those wherein $R^{11}$ is a $C_{1-18}$ alkyl group, preferably ethyl group, readily pass through lipophilic cytoplasmic membranes and are incorporated into the cells, and then the ester is hydrolyzed to give compounds having carboxyl group (compounds wherein $R^{11}$ is a hydrogen atom). Since the resulting compounds are highly hydrophilic, they cannot pass through lipophilic cytoplasmic membranes again, and thus they are not easily excreted from the inside of the cells. Therefore, those having a $C_{1-18}$ alkyl group as $R^{11}$ are useful as an agent for the measurement, per se, and they are also useful as a prodrug for transporting the agent for the measurement (compounds wherein $R^{11}$ is a hydrogen atom) into the cells at a high concentration. In addition, those wherein $R^{11}$ is a $C_{10-18}$ alkyl group are expected to localize in cytoplasmic membranes.

The measurement of fluorescence can be performed by a known conventional fluorescence measuring method (see, for example, publications such as Wiersma, J. H., Anal. Lett., 3, pp.123–132, 1970; Sawicki, C. R., Anal. Lett., 4, pp.761–775, 1971; Damiani, P. and Burini, G., Talanta, 8, pp.649–652, 1986; Misko, T. P., Anal. Biochem. 214, pp.11–16, 1993 and the like). In the method of measurement of nitric oxide according to the present invention, for example, it is preferred that light of about 565 nm is irradiated as excitation light, and fluorescence at about 580 nm is measured. By using lights having such wavelengths, efficient spectrometry can be performed by means of a fluorescence filter of an ordinarily used fluorescence microscope, and the measurement can be attained with high sensitivity without using a special filter.

When particularly high sensitivity measurement is required, the measurement of nitric oxide may be performed in the presence of an oxygen source. As the oxygen source, for example, oxygen, ozone, oxide compounds and the like may be used. Dissolved oxygen can generally be used as the oxygen source, and if necessary, oxygen gas may be introduced into a reaction system, or a reagent for generating oxygen (for example, hydrogen peroxide or the like) may be added. The oxide compounds are not particularly limited so long as they have an oxide bond from which oxygen atom is readily released, for example, N—O, S—O, and P—O. For example, PTIO (2-phenyl-4,4,5,5-tetramethylimidazoline-1-oxyl-3-oxide, Maeda, H., et al., J. Leuk. Biol., 56, pp.588–592, 1994; Akaike T., et al., Biochemistry, 32, pp.827–832, 1993) or its derivatives (carboxy-PTIO which is formed by introducing carboxyl group into the p-position of the phenyl group of PTIO etc.), triphenylphosphine oxide, triethylamine oxide and the like can be used.

Among the aforementioned oxide compounds, PTIO and its derivatives (for example, carboxy-PTIO etc.) are particularly preferred compounds, and they are readily obtained by those skilled in the art (listed in Tokyo Chemical Industry Co., Ltd., Organic Chemicals Catalog, 32, 1994 and the like). The oxide compounds, per se, may be used as a reagent, or those enclosed in liposomes or similar materials can also be used. An amount of the oxygen source is not particularly limited, and the amount may preferably be about 1 $\mu$M or more, more preferably about 10 to 30 $\mu$M, and most preferably about 10 to 20 $\mu$M at least based on nitric oxide to be measured. In the measurement for biological materials and the like, the oxygen source may preferably be added to a sample in an amount of about 10 to 20 $\mu$M; however, a necessary amount of the oxygen source may generally be supplied by dissolved oxygen. If the amount of the oxygen source is too small, measurement sensitivity may be reduced, and if the amount of the oxygen source is too much, fluorescence emission may be adversely affected. Therefore, it is preferred to predict the amount of nitric oxide to be measured beforehand by a preliminary experiment or a known method, and add the oxygen source in a suitable range of concentration. The reaction may be performed within a temperature range of 0 to 40° C.

EXAMPLES

The present invention will be more specifically explained with reference to the following examples. However, the scope of the present invention is not limited to the following examples. In the examples, "DAR-1" corresponds to the compound shown in the above scheme.

EXAMPLE 1

Production of DAR-1 [9-(2-carboxy-3,4-diaminophenyl)-6-diethylamino-3H-xanthen-3-ylidene]diethyl-iminium]

2,3-Dimethyl-6-nitroaniline was acetylated in acetic acid by using 1 equivalence of acetic anhydride, and the product was recrystallized from ethanol. The resulting 3-acetamido-4-nitroxylene was dissolved in boiled water containing magnesium sulfate. To the solution, 6 equivalences of potassium permanganate suspended in water was added in several portions, and the solution was refluxed until purple color disappeared. The hot reaction mixture was filtered and cooled, and then the filtrate was made acidic with hydrochloric acid and extracted with ethyl acetate. The resulting 3-acetamido-4-nitrophthalic acid was dehydrated in acetic anhydride using acetyl chloride. The reaction mixture was concentrated under reduced pressure, and then a small quantity of anhydrous methylene chloride was added to the residue and the deposited solid was collected by filtration to obtain 3-acetamido-4-nitrophthalic anhydride.

To the solution of 3-acetamido-4-nitrophthalic anhydride in xylene, N,N-diethylaminophenol dissolved in xylene was added dropwise over 30 minutes at a temperature slightly lower than a refluxing temperature, and the mixture was refluxed for 18 hours. After evaporation of xylene was evaporated, the residue was purified by silica gel column chromatography to obtain a 3-acetamido-4-nitrorhodamine derivative: [9-(2-carboxy- 3-amino-4-nitrophenyl) -6-diethylamino- 3H-xanthen- 3-ylidene] diethyl-iminium].

$C_{28}H_{31}N_4O_5$ F.W. 503.558; $^1$H-NMR (300 MHz, DMSO-$d_6$) δ 1.08 (t, 12H, J=6.8), 3.35 (q, 8H, J=6.8), 6.38 (d, 1H, J=8.6), 6.42 (m, 4H), 6.67 (d, 2H, J=9.8), 8.04 (s, 2H), 8.33 (d, 1H, J=8.6).

The 3-acetamido-4-nitrorhodamine derivative obtained above was deacetylated by refluxing in hydrochloric acid, and the resulting 3-amino-4-nitro-rhodamine was reduced in water using sodium sulfide and sodium hydrosulfide. After the reduction, the product was purified by silica gel column chromatography to obtain the target compound (DAR-1, m.p. 145° C., decomp.).

$C_{28}H_{33}N_4O_3$ F.W. 473.578; MS (EI) (m/z) M$^+$473; $^1$H-NMR (300 MHz, DMSO-$d_6$) δ 1.08 (t, 12H, J=6.78), 3.33 (m, 8H), 4.98 (s, 2H), 5.86 (s, 2H), 6.06 (d, 1H, J=7.68), 6.37–6.41 (m, 4H), 6.55 (d, 2H, J=8.61), 6.78 (d, 1H, J=7.68), 11.95 (s, 1H).

EXAMPLE 2

Production of DAR-1EE [9-(3,4-diamino-2-ethoxycarbonylphenyl)-6-diethylamino-3H-xanthen-3-ylidene]diethyliminium]

DAR-1 obtained in Example 1 was dissolved in a mixture of concentrated sulfuric acid and ethanol, and the resulting mixture was refluxed for 2 hours. The reaction mixture was poured into water, and subjected to a post-treatment in a conventional manner to obtain a crude product. The crude product was purified by silica gel column chromatography to obtain the desired compound.

$C_{30}H_{37}N_4O_3$ F.W. 501.628; MS (EI) (m/z) M$^+$501; $^1$H-NMR (300 MHz, CDCl$_3$) δ 0.66 (t, 3H, J=7.1), 1.33 (m, 12H), 3.61 (q, 8H, J=7.3), 4.19 (q, 2H, J=7.1), 4.55 (s, 2H), 6.05 (s, 2H), 6.33 (d, 1H, J=7.9), 6.74 (d, 2H, J=2.2), 6.83 (dd, 2H, J=9.7, 2.2), 6.94 (d, 1H, J=7.9), 7.45 (d, 2H, J=9.7).

EXAMPLE 3

Production of DAR-1T [9-(7-carboxybenzotriazol-6-yl)-6-diethylamino-3H-xanthen- 3-ylidene] diethyliminium]

DAR-1 obtained in Example 1 was dissolved in methanol, and NO gas was bubbled. The reaction mixture was concentrated under reduced pressure, and the residue was purified by silica gel column chromatography to obtain the target compound (m.p. 300° C. or higher).

$C_{28}H_{30}N_5O_3$ F.W. 484.558; MS (FAB) (m/z) M$^+$484; $^1$H-NMR (300 MHz, DMSO-$d_6$) δ 1.10 (t, 12H, J=6.4), 3.34 (m, 8H), 6.50–6.71 (m, 7H), 8.01 (d, 1H, J=8.1); Maximum wavelengths: Ex. 565 nm–Em. 580 nm.

EXAMPLE 4

Changes in Fluorescence Spectrum of a Compound of the Formula (I) by the Addition of Nitric Oxide 10 μM of DAR-1 was dissolved in 0.1 M phosphate buffer (pH 7.4). Nitric oxide at various concentrations (0.11 μM, 0.21 μM, 0.32 μM, 0.43 μM, 0.53 μM, and 0.64 μM) was added to the solution, and then changes in fluorescence spectrum were measured. The results are shown in FIG. 1. In the figure, (a) represents the excitation spectrum (Em. 580 nm), and (b) represents the fluorescence spectrum (Ex. 565 nm). It was observed that the strength of the maximum fluorescence wavelength was increased by the triazole compound (DAR-1T) produced in the reaction system as the concentration of nitric oxide increased.

EXAMPLE 5

Figure 2:
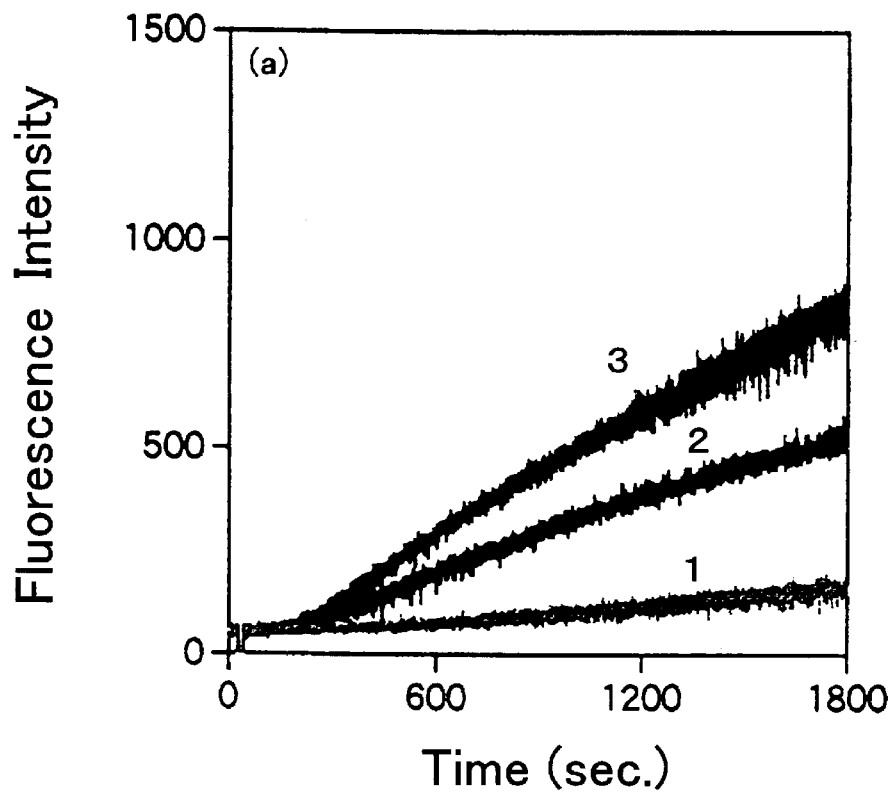
FIG. 2 depicts changes in fluorescence intensity of the compound of the formula (I) depending on the amount of generated nitric oxide. In the figure, (a) and (b) represent the results obtained by using NOC12 and NOC13, respectively. The curves 1, 2 and 3, and 1', 2' and 3' represent the results obtained by using the aforementioned NOCs a t concentrations of 10 μM, 50 μM and 100 μM, respectively.
Figure 2:
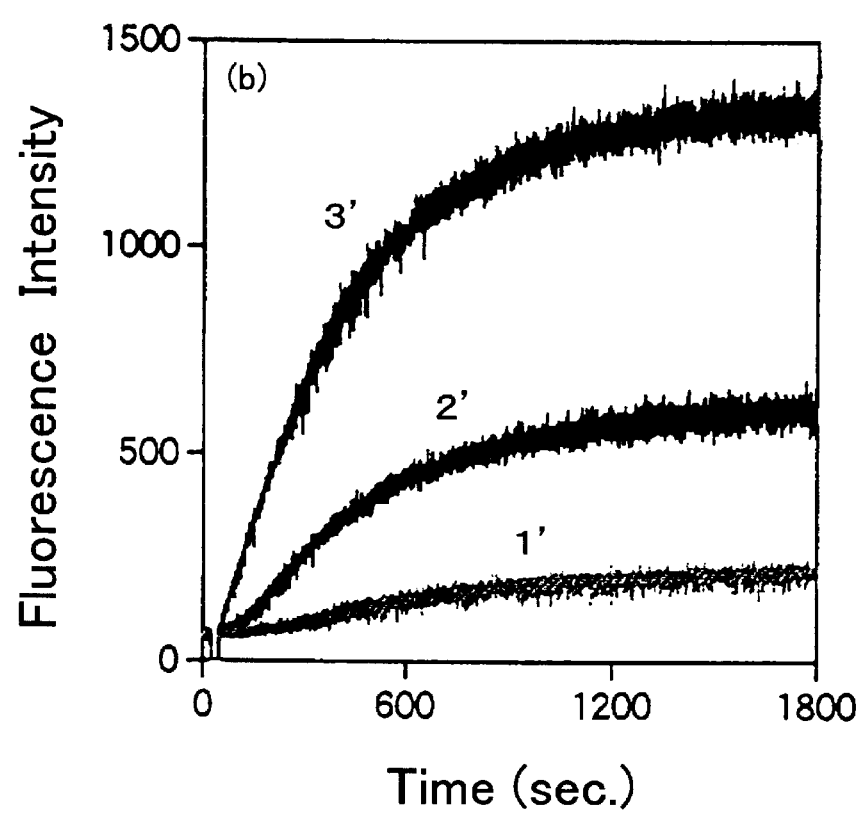

Changes in Fluorescence Intensity of the Compound of the Formula (I) Depending on the Amount of Nitric Oxide As a nitric oxide source, NOC-12 (having a half life of 327 minutes in 0.1 M phosphate buffer, pH 7.4 at 22° C.) and NOC-13 (13.7 minutes in the same conditions) were used among NOCs, which are the spontaneous NO generating agents (Hrabie J. A., J. Org. Chem., 58, pp.1472–1476, 1993). Nitrogen monoxide generated in a reaction mixture was allowed to react with DAR-1. NOCs at various concentrations (10 μM, 50 μM, 100 μM) was added to 10 μM of DAR-1, and allowed to react at 37° C. using 0.1 M phosphate buffer (pH 7.4) as a reaction solvent. The measurement of changes in fluorescence intensity was started 30 seconds before the start of the reaction by using measurement wavelengths at Ex. 565 nm–Em. 580 nm. The results are shown in FIG. 2. In the figure, (a) and (b) represent the results of the measurements using NOC12 and NOC13, respectively. The curves 1, 2 and 3, and 1', 2' and 3' represent the results obtained in the presence of the NOCs at concentrations of 10 μM, 50 μM and 100 μM, respectively. From these results, it is obvious that the triazole compound (DAR-1T) was produced from DAR-1 depending on the amount of generated nitric oxide, and changes in fluorescence intensity that correctly reflected nitric oxide concentration were observable.

EXAMPLE 6

Sensitivity Of the Compound of the Formula (I) for Nitric Oxide Measurement

Figure 3:
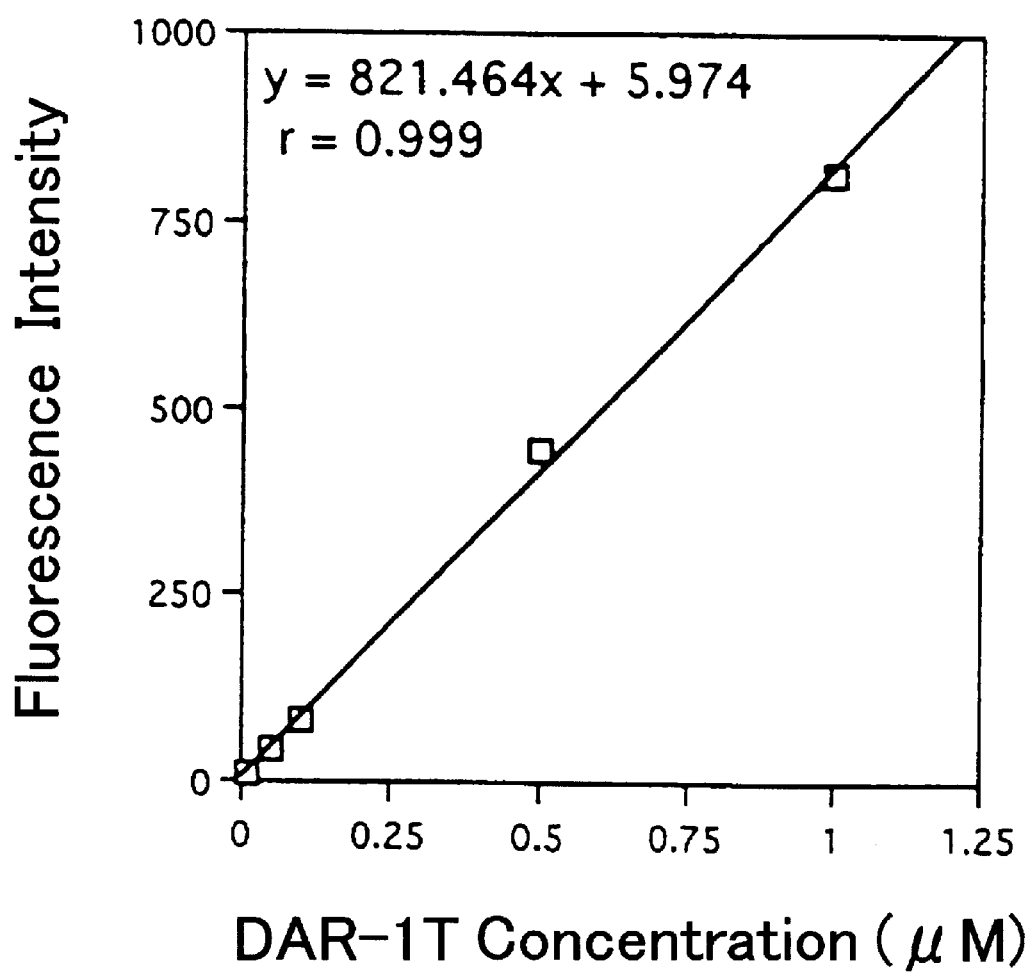
FIG. 3 shows correlation between fluorescence intensity and concentration of a compound (DAR-1T) of th e formula (II) (calibration curve).

A synthetic sample of the triazole compound, corresponding to the reaction product of DAR-1 with nitric oxide, was dissolved in 0.1 M phosphate buffer (pH 7.4). Increase in fluorescence intensity in a concentration-dependent manner was observed. The measurement wavelengths of fluorescence were set to Ex. 565 nm–Em. 580 nm. The results are shown in FIG. 3.

EXAMPLE 7

Changes in Sensitivity at Varying pHs

Figure 4:
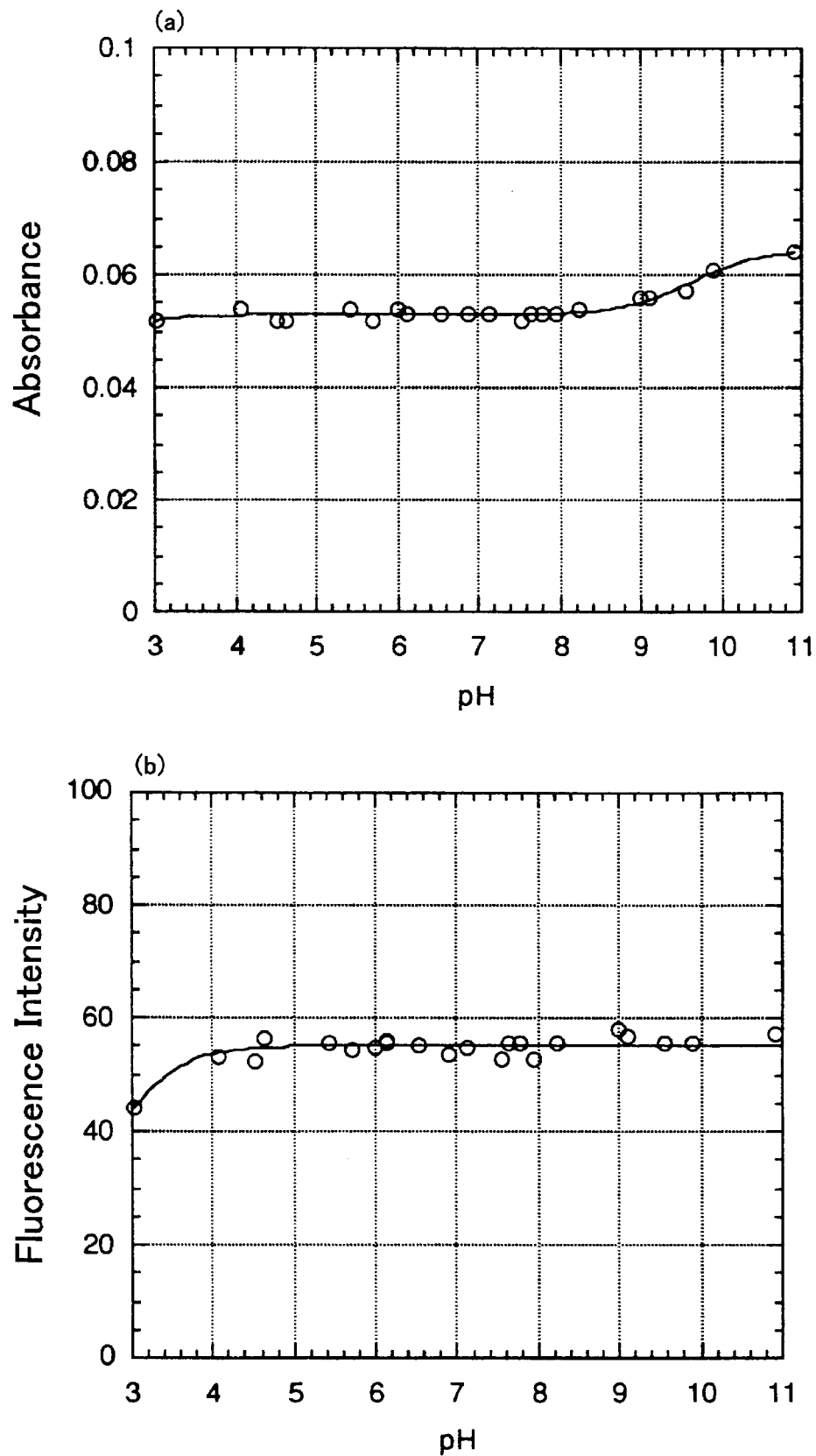
FIG. 4 shows results of changes in sensitivity of the compound of the formula (I) as a function of pH.

DAR-1T was dissolved in purified water to prepare a solution of a concentration of 100 μM. The solution was added to phosphate buffer (78 mM) adjusted to each pH at a final concentration of about 1 μM, and absorbance and fluorescence intensity were measured. The measurement wavelengths of fluorescence were set to Ex. 565 nm–Em. 580 nm. The results are shown in FIG. 4. In the figure, (a) represent the results of the absorptiometric measurement and (b) represents the results of fluorescence intensity measurement. From these results, it was observed that DAR-1T exhibited no changes in fluorescence intensity and maintained high sensitivity in the range from neutral to weakly acidic, approximately pH 4, conditions.

EXAMPLE 8

Imaging of Nitric Oxide Produced by Vascular Smooth Muscle Cells

Vascular smooth muscle cells derived from rat arota were cultured in a glass bottom dish, and stimulated with LPS (12.5 μg/ml), INF-γ (150 U/ml), IL-1β (25 U/ml) and TNF-α (30 ng/ml) to induce a nitric oxide synthase. The culture was continued for about 12 hours, and then the culture medium was changed to Krebs-Ringer-phosphate buffer (KRP) in which DAR-1EE was dissolved (Example 2, 10 μM) to allow uptake of DAF-1EE by the cells. The cells were cultured at 37° C. for 1 hour, and washed, and the culture medium was changed to KRP in which L-Arg or L-NMMA was dissolved. Changes in intracellular fluorescence with time was observed under a fluorescence microscope (Ex. 530–560 nm, Em. 550–610 nm, magnification: ×20).

Figure 5:
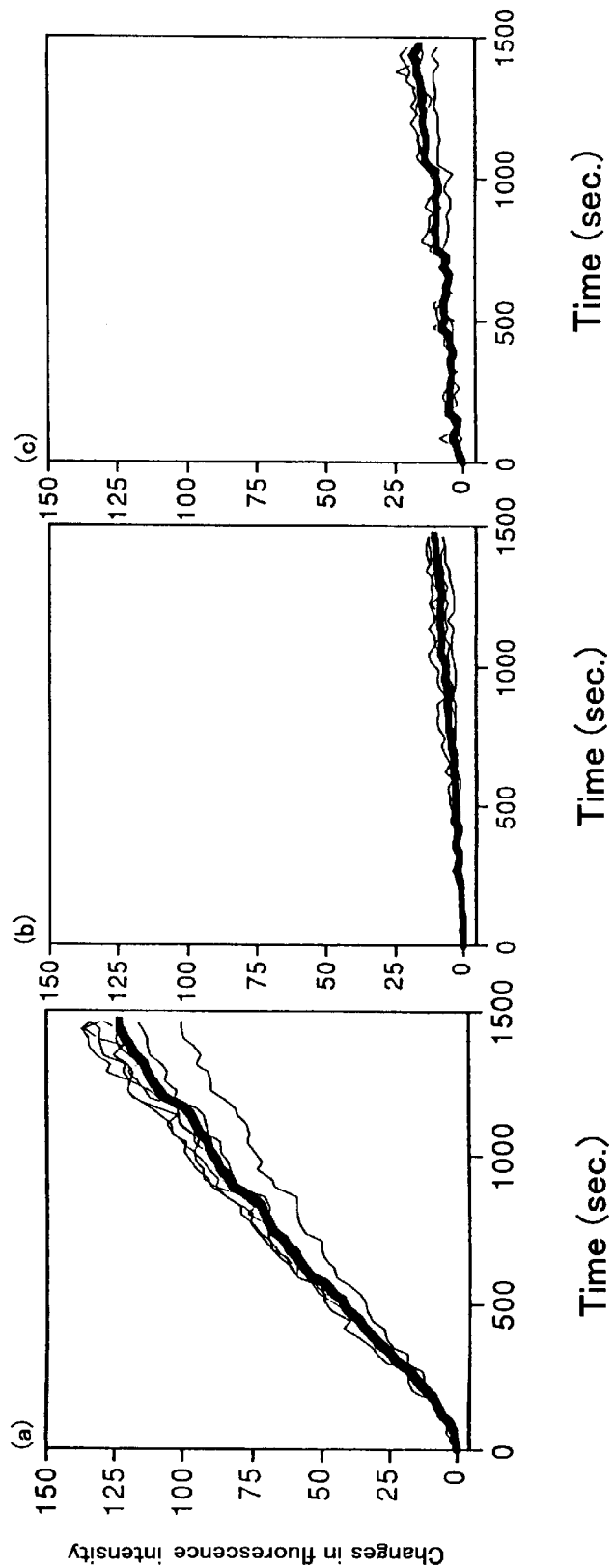
FIG. 5 shows results of measurement of nitric oxide present in individual cells. In the figure, (a) shows changes after replacement of a culture medium of stimulated cells with a culture medium containing 1 mM L-Arg (incubation: 35 minutes, nitric oxide-producing cells); (b) shows changes after replacement of a culture medium of non-stimulated cells with a culture e medium containing 1 mM L-A rg (incubation: 75 minutes, nitric oxide non-producing cells); and (c) shows changes after replacement of the culture medium of the step (a) with a culture medium containing 1 mM L-Arg+10 mM NMMA (incubation: 108 minutes, in the presence of NOS inhibitor). The normal lines represent fluorescence intensity of each cell and bold lines represent the averages thereof.

The results of the measurement of nitric oxide produced in each cell are shown in FIG. 5. Fluorescence intensity increased with time in the nitric oxide producing cells (a), whereas substantially no change in fluorescence intensity was observed in the cells producing no nitric oxide (non-stimulated, b) as well as in the cells added with the NOS inhibitor (c). From these results, it was confirmed that DAR-1EE was uptaken into the cells and hydrolyzed, and then DAR-1 reacted with nitric oxide to emit fluorescence.

INDUSTRIAL APPLICABILITY

The compounds of the present invention are useful as an agent for nitric oxide measurement. The compounds of the formula (I) according to the present invention have a characteristic feature that they efficiently react with nitric oxide to give fluorescent compounds of the formula (II). The compounds of the formula (II) emit strong fluorescence by irradiation with excitation light of a longer wavelength not harmful to living tissues or cells, and accordingly, they are characterized to achieve correct measurement of intracellular nitric oxide of individual cells. In particular, the compounds of the formula (II) according to the present invention have characteristics that they are detectable in a fluorescence wavelength range that is hardly influenced by the autofluorescence of the cells, and their fluorescence intensity is not attenuated under acidic conditions.

What is claimed is:

1. A compound represented by the following general formula:

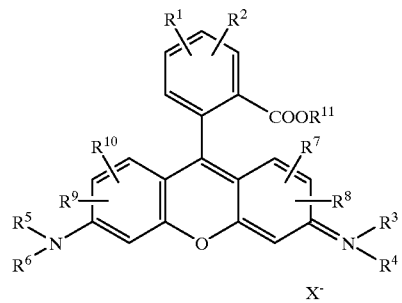

wherein $R^1$ and $R^2$ represent amino groups present at adjacent positions each other on the phenyl ring; $R^3$, $R^4$, $R^5$ and $R^6$ each independently represent a $C_{1-6}$ alkyl group; $R^7$, $R^8$, $R^9$ and $R^{10}$ each independently represent a hydrogen atom, a $C_{1-6}$ alkyl group, an allyl group, or a halogen atom; $R^{11}$ represents a hydrogen atom or a $C_{1-18}$ alkyl group; and $X^-$ represents an anion.

2. The compound according to claim 1, wherein $R^3$, $R^4$, $R^5$ and $R^6$ are ethyl groups; and $R^7$, $R^8$, $R^9$ and $R^{10}$ are hydrogen atoms.

3. An agent for nitric oxide measurement which comprises the compound according to claim 1.

4. A compound represented by the following general formula:

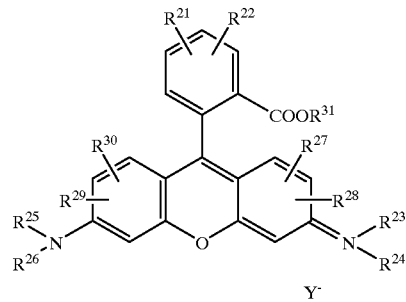

wherein $R^{21}$ and $R^{22}$ are present at adjacent positions on the phenyl ring and bind to each other to form a group represented as —N=N—NR$^{41}$— that forms a ring, wherein $R^{41}$ represents hydrogen atom, a $C_{1-18}$ alkyl group, or an aralkyl group which may be substituted, or $R^{21}$ and $R^{22}$ represent a combination of amino group and nitro group present at adjacent positions on the phenyl ring; $R^{23}$, $R^{24}$, $R^{25}$ and $R^{26}$ independently represent a $C_{1-6}$ alkyl group; $R^{27}$, $R^{28}$, $R^{29}$ and $R^{30}$ each independently represent hydrogen atom, a $C_{1-6}$ alkyl group, an allyl group, or a halogen atom; $R^{31}$ represents hydrogen atom or a $C_{1-18}$ alkyl group; and $Y^-$ represents an anion.

5. A method for measurement of nitric oxide, which comprises:

(1) a step of allowing the compound according to claim 1 to react with nitric oxide, and (2) a step of detecting a compound produced in the step (1).

* * * * *

UNITED STATES PATENT AND TRADEMARK OFFICE
CERTIFICATE OF CORRECTION

PATENT NO.    : 6,201,134 B1                          Page 1 of 1
DATED         : March 13, 2001
INVENTOR(S)   : T. Nagano et al.

It is certified that error appears in the above-identified patent and that said Letters Patent is hereby corrected as shown below:

<u>Title page,</u>
Item [56], References Cited, the following FOREIGN PATENT DOCUMENT was omitted and should be included:
-- 9-43153   2/1997   Japan --

Signed and Sealed this

Second Day of April, 2002

*Attest:*

*Attesting Officer*

JAMES E. ROGAN
*Director of the United States Patent and Trademark Office*